United States Patent [19]

Roth et al.

[11] Patent Number: 4,920,974

[45] Date of Patent: May 1, 1990

[54] METHOD OF OBTAINING CERVICAL CULTURE SPECIMENS AND DEVICE AND KIT THEREFOR

[75] Inventors: Alex T. Roth, Foster City, Calif.; Richard M. Soderstrom, Seattle, Wash.

[73] Assignee: EndoTherapeutics, Menlo Park, Calif.

[21] Appl. No.: 181,217

[22] Filed: Apr. 13, 1988

[51] Int. Cl.⁵ .............................................. A61B 10/00
[52] U.S. Cl. .................................... 128/759; 604/358; 604/393
[58] Field of Search .................... 128/749–759, 128/304, 361; 604/54–55, 292, 1–2, 328, 330–331, 358, 393, 402; 206/69, 569–570, 549, 438–441

[56] References Cited

U.S. PATENT DOCUMENTS

| | | | |
|---|---|---|---|
| 2,844,150 | 7/1958 | Draghi | 128/759 |
| 3,658,065 | 4/1972 | Hirsch | 604/327 |
| 3,672,351 | 6/1972 | Ubersax et al. | 128/759 X |
| 3,913,564 | 10/1975 | Freshley | 128/759 |
| 3,939,044 | 2/1976 | Wilkins et al. | 128/759 X |
| 4,175,008 | 11/1979 | White | 128/759 X |
| 4,241,828 | 12/1980 | Bourdelle et al. | 206/306 |
| 4,244,057 | 1/1981 | Burnham | 604/358 X |
| 4,327,744 | 5/1982 | Smith | 128/749 X |
| 4,409,988 | 10/1983 | Greenspan | 128/759 |
| 4,465,078 | 8/1984 | Manning et al. | 128/759 |

*Primary Examiner*—Angela D. Sykes
*Attorney, Agent, or Firm*—Irell & Manella

[57] ABSTRACT

A method is provided for obtaining cervical cell culture specimens. The method makes use of a test device which may be used in conjunction with the manual cervical examination prior to delivery. The device includes an elastically resilient sheath adapted to grip a finger and a sterile pad of absorbent material on one end adapted to collect and retain the cell culture specimen. A kit is provided as well, the kit including a support member for maintaining the device in an unrolled, elongated, unrolled configuration and is designed so as to maintain sterile conditions and minimize contamination during storage and transport.

10 Claims, 2 Drawing Sheets

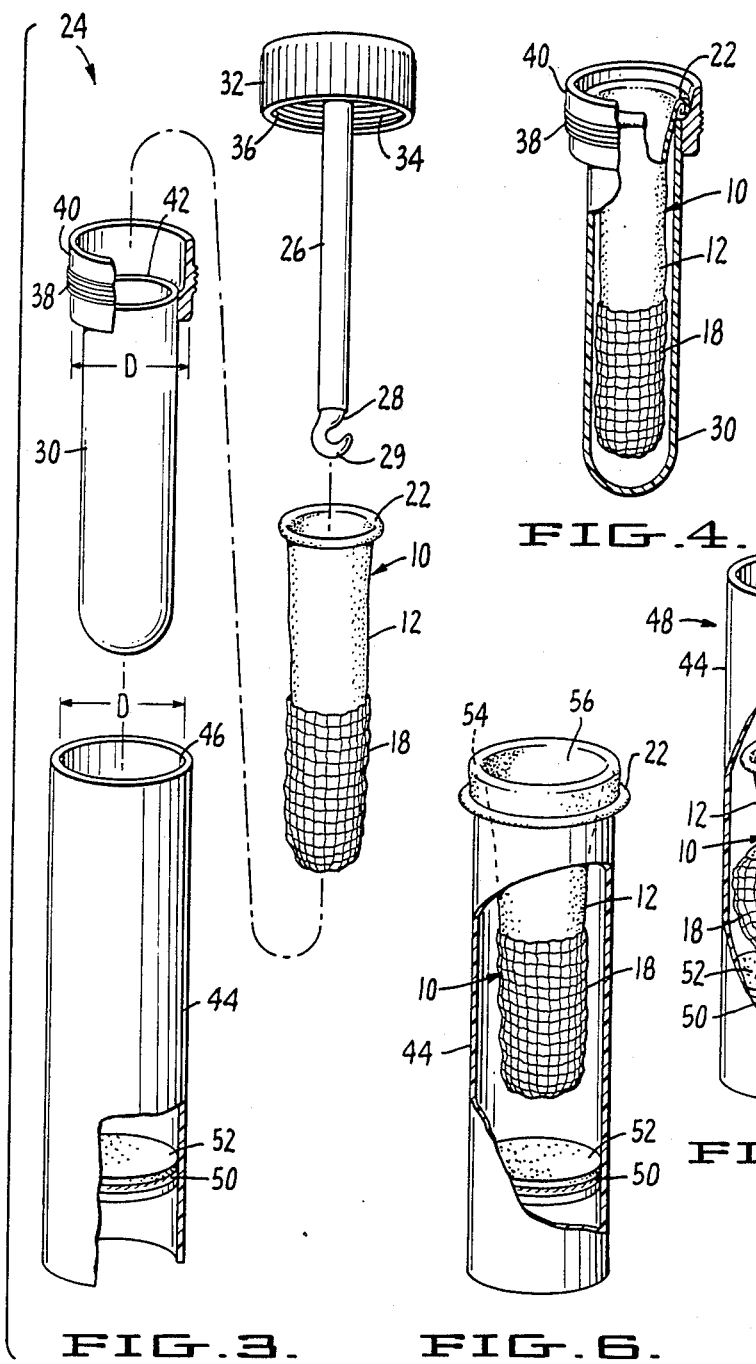

METHOD OF OBTAINING CERVICAL CULTURE SPECIMENS AND DEVICE AND KIT THEREFOR

FIELD OF THE INVENTION

This invention relates generally to methods and devices for obtaining cell culture specimens, and in particular relates to an improved method and test for obtaining cervical culture specimens. One important use of the present invention is to aid in the detection of the asymptomatic presence of herpes virus in a patient immediately prior to childbirth, thus enabling prevention and/or early treatment of neonatal herpes in the newborn child. In addition, the device is generally useful in applications where digital cell sample gathering is preferable to instrumented techniques.

BACKGROUND OF THE INVENTION

The presence of herpes viral infection in prepartum women is an indication for caesarean section, as neonatal herpes may be acquired through the birth canal. Because failure to diagnose neonatal herpes or to treat the disease at an early stage can be fatal to the newborn child, it is extremely important to detect the presence of herpes virus infection immediately prior to a patient's giving birth. Since, at this point in time, the herpes virus remains a disorder of epidemic proportions, the occurrence of neonatal herpes is not at all infrequent.

It would thus be desirable to screen women prior to giving birth—i.e., at the time of admission to the hospital for labor and delivery—as well as during pregnancy. Screening immediately prior to delivery, however, has proved problematic. This is because the logistics of obtaining, culturing and testing a cervical cell specimen immediately prior to delivery do not, typically, allow for detection of the herpes virus in time to perform a caesarean section. The difficulty is in part due to the fact that present devices and methods of obtaining cervical cell specimens require a separate procedure which is in addition to the physician's or nurse's manual examination prior to delivery.

Most of the commercially available devices for obtaining cervical culture samples are "swabs", i.e., elongated rods having at one end a mound of absorbent cotton or other material for taking of the sample. For example, U.S. Pat. No. 3,386,549 to Barr et al. discloses a diagnostic swab having an elongated handle or stick and, at its distal end, a culture medium. Similarly, U.S. Pat. No. 3,626,470 to Antonides et al. describes a diagnostic device for obtaining cervical cell specimens which, at the distal end of an elongated handle, is provided with a sample collector of polysiloxane foam impregnated with a proteolytic enzyme. U.S. Pat. Nos. 3,586,380, 3,776,219 and 4,023,559 to Albeckoff, Brown and Gaskell, respectively, also show swab-like sampling devices for taking cervical cell samples.

A further drawback with present cervical culturing procedures is the time required for culturing and analysis of the cervical cells. While no method is presently available for expediting the analytical procedure, it is expected that upon development of monoclonal antibodies to herpes viral antigens, a rapid immunoassay, useful in conjunction with the present device and method, will be available.

Thus, the present invention addresses one of the aforementioned problems by providing a method for obtaining a cervical culture specimen that, as will be described, may be combined with a physician's manual examination prior to delivery. Alternatively, the nurses who typically perform the digital palpation of the cervix over the course of labor may also readily collect the sample without instrumentation.

SUMMARY OF THE INVENTION

Accordingly, it is an object of the present invention to provide a disposable test device for obtaining cervical culture specimens, which device is adapted to fit a finger and may thus be used in the course of a manual examination prior to delivery.

It is another object of the present invention to provide a kit for obtaining, sealing, and transporting a cervical culture specimen, the kit including a means for preventing contamination of the aforementioned device after obtaining the specimen as well as a means for maintaining the device in a configuration adapted to facilitate analysis.

It is still another object of the present invention to provide a method for a physician or nurse to obtain a cervical culture specimen using the aforementioned device.

It is a further object of the present invention to provide a method for a physician or nurse to detect the presence of herpes virus on a patient's cervix.

Additional objects, advantages and novel features of the invention will be set forth in part in the description which follows, and in part will become apparent to those skilled in the art on examination of the following, or may be learned by practice of the invention.

In one aspect of the invention, a test device is provided for obtaining a cervical culture specimen, the device comprised of an elastically flexible sheath having at one end a sterile pad of absorbent material adapted to collect and retain the culture specimen. The elastically flexible sheath is dimensioned so as to fit over and grip a finger; thus, after—or during—a manual examination, the cervical area may be traversed with the aforementioned pad so as to collect the culture specimen.

In another aspect of the invention, a kit is provided for containing and transporting the cervical culture specimen. The kit includes a support member structured so as to fit within the device and maintain the elastically flexible sheath in an unrolled, elongated configuration. The kit also includes a container adapted to receive the test device on the support member as well as a means for preventing contamination.

In another aspects of the invention, methods are provided for obtaining and transporting culture specimens, and cervical culture specimens in particular.

BRIEF DESCRIPTION OF THE DRAWINGS

FIG. 3 is an exploded side view of the kit for obtaining a cervical culture specimen.

FIG. 4 is a partially cut away, side view of the test device, shown within the kit's "inner" container.

FIG. 5 illustrates an alternative embodiment of the invention, and is a partially cut away, side view of the test device, shown within the kit's "outer" container.

FIG. 6 is a side view of another alternative embodiment of the invention, showing the test device prior to use, again within the kit's outer container.

DETAILED DESCRIPTION OF THE INVENTION

Figures 1, 2:
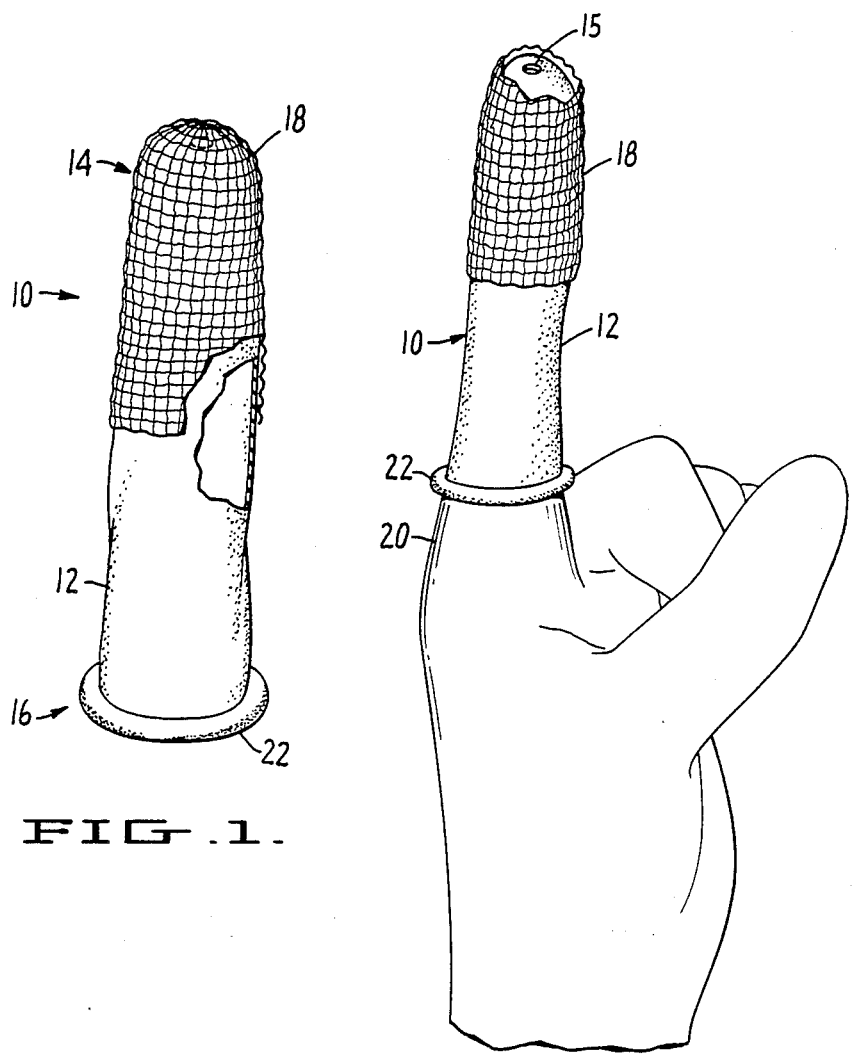
FIGS. 1 and 2 are side views of the test device, FIG. 2 showing the device positioned on a finger.

Turning now to the drawings, FIG. 1 illustrates the test device generally at 10, including elastically flexible sheath 12 which in one embodiment is closed at its distal end 14 and open at its proximal end 16. In an alternative, preferred embodiment, the distal end 14 of the sheath is provided with a small opening 15. Flexible sheath 12 is sized and shaped so as to conform to and grip a finger. Affixed to the sheath at its distal end is a sterile pad 18 of absorbent material adapted to collect and retain a cell culture specimen. The sheath is typically fabricated from an inexpensive, water-impermeable rubbery material such as natural rubber (latex) or a synthetic material such as polyurethane or the like. Pad 18 is typically an absorptive felt, fabric or gauze material. It can be made of natural fibers, most typically, cotton, or it can be made of synthetic materials such as cellulose. The pad should be compliant, flexible, and relatively thin so as to minimize patient discomfort as well as interference with other aspects of the pre-birth examination process. While pad 18 may be affixed to sheath 16 in a variety of ways, a preferred method is by using a suitable, waterproof adhesive. All of the materials of the device 10 should be nontoxic, pharmaceutically acceptable and capable of withstanding sterilization conditions, be they ethylene oxide sterilization, radiation sterilization or autoclaving.

The aperture 15 present in the preferred embodiment at the distal end of the flexible sheath enhances flow of sample and, ultimately, growth medium, within and through pad 18. After use, such a configuration also facilitates mixing of the cell culture specimen with growth medium, as will be discussed.

FIG. 2 shows the device as positioned on a finger 20, typically over a physician's or nurse's glove. Elasticized ring 22 at the base of the device facilitates gripping of the finger and enables the device to be rolled off of the finger after obtaining the culture specimen.

FIG. 3 illustrates in exploded form a kit 24 for containing and transporting the cervical culture specimen. In a preferred embodiment, kit 24 includes test device 10, a support 26, an inner container 30 which threadably engages to and seals support 26 and an outer container 44. Tip 28 at the distal end of support member 26 is designed to be inserted into the open end of device 10 after the necessary culture is obtained, so that support member 26 unrolls sheath 12 and maintains it in an elongated, unrolled configuration. Transport of the device in such a configuration facilitates analysis by allowing for easy access to specimen on the pad. The transport kit also allows the cell culture specimen to survive transport to the clinical laboratory. The transport tube, outer container 44, is in a preferred embodiment dimensioned so that it can be placed in standard vortexing and centrifuging machines during the analytical procedures carried out in the laboratory.

Inner container 30 is adapted to receive the unrolled test device on support member 26. As may be seen in FIG. 4, the test device is dimensioned in both length and width so that it "nests" within the inner container. In a preferred embodiment, tip 28 is provided with an arcuate hook 29 adapted to facilitate removal of the test device from the container after transport to the laboratory for analysis. Hook 29, as illustrated in FIG. 3, is actually of a somewhat bulbous shape, so that support 26 may be used to knead the growth medium through pad 18 to facilitate mixing of the cell culture specimen with the growth medium.

The kit includes a means for preventing contamination which, in a preferred embodiment, is a cap 32 provided with threads 34 on its interior side walls 36. The cap seals inner container 30 by threaded engagement with the external threads 38 on sealing collar 40. As may be seen in FIGS. 3 and 4, sealing collar 40 encircles mouth 42 of the inner container. The inner surfaces of sealing collar 40 and mouth 42 must be of a smoothness sufficient to prevent removal of specimen from test device 10 as it is inserted into inner container 30. Maximum diameter D of the sealing collar (see FIG. 3) is just slightly less than the diameter of second, outer container 44 into which the inner container is placed. Outer container 44 is thus automatically sealed upon insertion of inner container 30, i.e., because of the sealing friction fit between collar 40 and mouth 46 of the outer container.

In an alternative embodiment, illustrated in FIG. 5, the device may simply be placed in one container 48. In such a case, base 50 within outer container 44 is provided on its interior face 52 with growth medium, i.e., nutrients essential to maintain the viability of the specimen until analysis thereof. The container is sealed with a suitable means until removal of the device for analysis.

FIG. 6 illustrates another alternative embodiment of the invention, in which the elasticized ring 22 of test device 10 is provided stretched across and over mouth 54 of container 44, while the length of the test device is maintained within the container. In such a configuration, the device can be placed on a gloved finger of the examining health care professional simply by pushing into open end 56 of the test device down into the container. Elasticized ring 22 of the device is rolled off of the container mouth 54, allowing the test device to grip the distal part of the finger.

The method of obtaining the cervical culture specimen using the present device is thus as follows. The device is placed on the finger of the examining health care professional, over his or her examination glove, either by unrolling or by pushing into the open end of the test device configured as shown in FIG. 6. After completion of the manual cervical examination—or during the examination—the cervical area of the patient is traversed with the sterile pad at the tip of the finger. The device is removed from the finger, most easily by unrolling. At this point, the device is either unrolled and emplaced within the nexted containers as illustrated in FIG. 3 or placed in one container as illustrated in FIG. 5. Where, in the preferred embodiment, the method further involves enabling the physician to detect the presence of herpes on the cervix, the culture specimen obtained is analyzed for the presence of the virus.

Several additional aspects of the present device, kit and methods should be noted. First, a primary advantage of the invention is to enable a physician or nurse to obtain the culture specimen at the time the manual examination is carried out. This reduces the time involved which is obviously critical in the hours just prior to delivery. Second, the sterile pad provided to collect and retain the cervical culture specimen has far more surface area than the conventional swab devices. The quantity of virus which may be collected is thus substantially increased, correspondingly improving the reliability of the test, i.e., so that low levels of virus, as might be expected in the asymptomatic patient, can be detected. Finally, while the invention has been described in terms of obtaining cervical culture specimens, clearly the device and kit may be used in conjunction with obtaining virtually any type of specimen from a body cavity, either by the patient or by an examining physician.

It is to be understood that while the invention has been described in terms of the preferred specific embodiments thereof, that the foregoing description is intended to illustrate and not limit the scope of the invention. Other aspects, advantages and modifications within the scope of the invention will be apparent to those skilled in the art to which the invention pertains.

I claim:

1. A kit for obtaining a cervical culture specimen, comprising:
   (a) a disposable test device comprising: (i) an elastically flexible sheath adapted to grip a finger, the sheath having a distal end and a proximal end, and being substantially closed but including a small aperture at its distal end and open at its proximal end; and (ii) a sterile pad of absorbent material affixed to said distal end of said sheath over said aperture and adapted to collect and retain said specimen;
   (b) a support member having a first, distal end, and a second, proximal end, structured so as to fit within said sheath so that, after obtaining said culture specimen, said test device is maintained in an elongated, unrolled configuration on said support member with said distal end of said support member inserted within and substantially aligned with said distal end of said test device;
   (c) a first, inner container adapted to receive said test device on said support member, said container having an open, proximal end, and a closed, distal end; and
   (d) a means for preventing contamination of said inner container,
   wherein said means for preventing contamination comprises a cap which seals said inner container, and wherein the proximal end of said support member is affixed to said cap such that said support member extends perpendicularly therefrom;
   and wherein said aperture is positioned adjacent said sterile pad for enhancing flow of the cell culture specimen therethrough and for facilitating mixture of the specimen with growth medium.

2. The kit of claim 1, wherein said cap is threadably engageable with a sealing collar affixed to the proximal end of said inner container.

3. The kit of claim 2, wherein said means for preventing contamination further comprises a second, outer container adapted to enclose said inner container, wherein said outer container has an open, proximal end and a closed, distal end.

4. The kit of claim 3, wherein said sealing collar on said inner container is adapted to provide a sealing fit with the open, proximal end of said outer container upon insertion of said inner container into said outer container.

5. The kit of claim 1, wherein said sterile pad is comprised of absorbent felt, fabric or gauze.

6. The kit of claim 1, wherein said sheath is provided at its open, proximal end with an elasticized ring adapted to facilitate gripping of and rolling on and off of a finger.

7. The kit of claim 6, wherein said elasticized ring is provided circumferentially stretched and fitted around the mouth of a tubular container.

8. The kit of claim 1, further including a means for removing said test device from said inner container.

9. A disposable test device for obtaining a cervical culture specimen, comprising: (a) an elastically flexible sheath adapted to grip a finger, the sheath having a distal end and a proximal end, and being substantially closed at its distal end and open at its proximal end; (b) a sterile, flexible pad of absorbent material affixed to and integral with said distal end of said sheath adapted to collect and retain said specimen; and (c) an elasticized ring at said open, proximal end of said sheath adapted to facilitate gripping of and rolling on and off of a finger, wherein said test device is elastically flexible in its entirety, and wherein said distal end of said sheath is povided with an aperture sized for enhancing fluid flow within and through said sterile pad and for facilitating mixture of the specimen with a growth medium, and wherein said pad is positioned over said aperture.

10. A kit for obtaining a cervical culture specimen, comprising:
   (a) a disposable test device comprising: (i) an elastically flexible sheath adapted to grip a finger, the sheath having a distal end and a proximal end, and being substantially closed but including a small aperture at its distal end and open at its proximal end; and (ii) a sterile pad of absorbent material affixed to said distal end of said sheath over said aperture and adapted to collect and retain said specimen;
   (b) a support member having a first, distal end, and a second, proximal end, structured so as to fit within said sheath so that, after obtaining said culture specimen, said test device is maintained in an elongated, unrolled configuration on said support member with said distal end of said support member inserted within and substantially aligned with said distal end of said test device;
   (c) a first, inner container adapted to receive said test device on said support member, said container having an open, proximal end, and a closed, distal end; and
   (d) a means for preventing contamination of said inner container,
   wherein said means for preventing contamination comprises a cap which seals siad inner container, and wherein the proximal end of said support member is affixed to said cap such that said support member extends perpendicularly therefrom;
   and wherein said aperture is positioned adjacent said sterile pad for enhancing flow of the cell culture specimen therethrough and for facilitating mixture of the specimen with growth medium;
   further including a means for removing said test device from said inner container; and,
   wherein said means for removing comprises an arcuate hook at the distal end of said support member.

* * * * *